United States Patent [19]

Cherpeck

[11] Patent Number: 5,407,452
[45] Date of Patent: Apr. 18, 1995

[54] FUEL COMPOSITIONS CONTAINING POLY(OXYALKYLENE) AROMATIC ESTERS

[75] Inventor: Richard E. Cherpeck, Cotati, Calif.

[73] Assignee: Chevron Chemical Company, San Francisco, Calif.

[21] Appl. No.: 98,586

[22] Filed: Jul. 28, 1993

[51] Int. Cl.⁶ .................................................. C10L 1/18
[52] U.S. Cl. ......................................... 44/399; 560/50
[58] Field of Search .................. 44/323, 385, 388, 391, 44/399, 412, 413, 426, 438; 560/50

[56] References Cited

U.S. PATENT DOCUMENTS

| | | | |
|---|---|---|---|
| 2,714,607 | 8/1955 | Matter | 260/471 |
| 2,714,608 | 8/1955 | Matter | 260/471 |
| 2,714,609 | 8/1955 | Matter | 260/471 |
| 2,714,610 | 8/1955 | Matter | 260/471 |
| 3,149,933 | 9/1964 | Ley et al. | 44/75 |
| 3,434,814 | 3/1969 | Dubeck et al. | 44/69 |
| 4,320,020 | 3/1982 | Lange | 252/51.5 |
| 4,320,021 | 3/1982 | Lange | 252/51.5 |
| 4,328,322 | 5/1982 | Baron | 521/163 |
| 4,347,148 | 8/1982 | Davis | 252/51.5 |
| 4,386,939 | 6/1983 | Lange | 44/63 |
| 4,515,981 | 5/1985 | Otani et al. | 560/50 |
| 5,039,775 | 8/1991 | Oyaizu | 528/68 |
| 5,081,295 | 1/1992 | Reardan et al. | 564/163 |
| 5,086,153 | 2/1992 | Oyaizu | 528/68 |
| 5,090,914 | 2/1992 | Reardan et al. | 435/188 |
| 5,103,039 | 4/1992 | Reardan et al. | 560/33 |
| 5,157,099 | 10/1992 | Reardan et al. | 528/68 |
| 5,211,721 | 5/1993 | Sung et al. | 44/389 |

FOREIGN PATENT DOCUMENTS 0580664 8/1959 Canada.
0812360 4/1959 United Kingdom.

*Primary Examiner*—Prince Willis, Jr.
*Assistant Examiner*—Cephia D. Toomer
*Attorney, Agent, or Firm*—C. J. Caroli

[57] ABSTRACT

Fuel compositions containing a major amount of hydrocarbons boiling in the gasoline or diesel range and an effective deposit-controlling amount of a poly(oxyalkylene) aromatic ester having the formula:

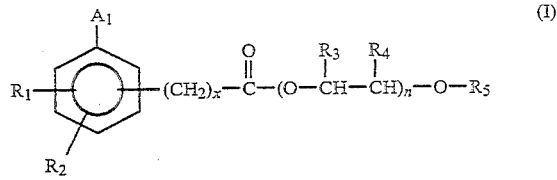

(I)

where $A_1$ is nitro, amino, N-alkylamino wherein the alkyl group contains 1 to 6 carbon atoms, or N,N-dialkylamino wherein each alkyl group independently contains 1 to 6 carbon atoms; $R_1$ and $R_2$ are independently hydrogen, hydroxy, lower alkyl, or lower alkoxy; $R_3$ and $R_4$ are independently hydrogen or lower alkyl and each $R_3$ and $R_4$ is independently selected in each $-O-CHR_3-CHR_4-$ unit; $R_5$ is hydrogen, alkyl having 1 to 100 carbon atoms, phenyl, aralkyl having 7 to 100 carbon atoms or alkaryl having 7 to 100 carbon atoms, or an acyl group of the formula:

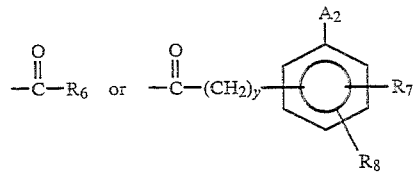

where $R_6$ is alkyl having 1 to 30 carbon atoms, phenyl, aralkyl having 7 to 36 carbon atoms or alkaryl having 7 to 36 carbon atoms; $R_7$ and $R_8$ are independently hydrogen, hydroxy, lower alkyl, or lower alkoxy; $A_2$ is a nitro, amino, N-alkylamino wherein the alkyl group contains 1 to 6 carbon atoms, or N,N-dialkylamino wherein each alkyl group independently contains 1 to 6 carbon atoms; n is an integer from 5 to 100; and x and y are each independently integers from 0 to 10.

32 Claims, No Drawings

FUEL COMPOSITIONS CONTAINING POLY(OXYALKYLENE) AROMATIC ESTERS

BACKGROUND OF THE INVENTION

1. Field of the Invention

This invention relates to poly(oxyalkylene) aromatic esters and to fuel compositions containing poly(oxyalkylene) aromatic esters. More particularly, this invention relates to poly(oxyalkylene) aromatic esters having a nitro, amino, N-alkylamino or N,N-dialkylamino substituent on the aromatic moiety and to the use of such compounds in fuel compositions to prevent and control engine deposits.

2. Description of the Related Art

It is well known that automobile engines tend to form deposits on the surface of engine components, such as carburetor ports, throttle bodies, fuel injectors, intake ports and intake valves, due to the oxidation and polymerization of hydrocarbon fuel. These deposits, even when present in relatively minor amounts, often cause noticeable driveability problems, such as stalling and poor acceleration. Moreover, engine deposits can significantly increase an automobile's fuel consumption and production of exhaust pollutants. Therefore, the development of effective fuel detergents or "deposit control" additives to prevent or control such deposits is of considerable importance and numerous such materials are known in the art.

For example, amino phenols are known to function as detergents/dispersants, antioxidants and anti-corrosion agents when used in fuel compositions. U.S. Pat. No. 4,320,021, issued Mar. 16, 1982 to R. M. Lange, for example, discloses amino phenols having at least one substantially saturated hydrocarbon-based substituent of at least 30 carbon atoms. The amino phenols of this patent are taught to impart useful and desirable properties to oil-based lubricants and normally liquid fuels. Similar amino phenols are disclosed in related U.S. Pat. No. 4,320,020, issued Mar. 16, 1982 to R. M. Lange.

Similarly, U.S. Pat. No. 3,149,933, issued Sep. 22, 1964 to K. Ley et al., discloses hydrocarbon-substituted amino phenols as stabilizers for liquid fuels.

U.S. Pat. No. 4,386,939, issued Jun. 7, 1983 to R. M. Lange, discloses nitrogen-containing compositions prepared by reacting an amino phenol with at least one 3- or 4-membered ring heterocyclic compound in which the hetero atom is a single oxygen, sulfur or nitrogen atom, such as ethylene oxide. The nitrogen-containing compositions of this patent are taught to be useful as additives for lubricants and fuels.

Nitro phenols have also been employed as fuel additives. For example, U.S. Pat. No. 4,347,148, issued Aug. 31, 1982 to K. E. Davis, discloses nitro phenols containing at least one aliphatic substituent having at least about 40 carbon atoms. The nitro phenols of this patent are taught to be useful as detergents, dispersants, antioxidants and demulsifiers for lubricating oil and fuel compositions.

Similarly, U.S. Pat. No. 3,434,814, issued Mar. 25, 1969 to M. Dubeck et al., discloses a liquid hydrocarbon fuel composition containing a major quantity of a liquid hydrocarbon of the gasoline boiling range and a minor amount sufficient to reduce exhaust emissions and engine deposits of an aromatic nitro compound having an alkyl, aryl, aralkyl, alkanoyloxy, alkoxy, hydroxy or halogen substituent.

More recently, certain poly(oxyalkylene) esters have been shown to reduce engine deposits when used in fuel compositions. U.S. Pat. No. 5,211,721, issued May 18, 1993 to R. L. Sung et al., for example, discloses an oil soluble polyether additive comprising the reaction product of a polyether polyol with an acid represented by the formula RCOOH in which R is a hydrocarbyl radical having 6 to 27 carbon atoms. The poly(oxyalkylene) ester compounds of this patent are taught to be useful for inhibiting carbonaceous deposit formation, motor fuel hazing, and as ORI inhibitors when employed as soluble additives in motor fuel compositions.

Poly(oxyalkylene) esters of amino- and nitrobenzoic acids are also known in the art. For example, U.S. Pat. No. 2,714,607, issued Aug. 2, 1955 to M. Matter, discloses polyethoxy esters of aminobenzoic acids, nitrobenzoic acids and other isocyclic acids. These polyethoxy esters are taught to have excellent pharmacological properties and to be useful as anesthetics, spasmolytics, analeptics and bacteriostatics. U.S. Pat. Nos. 2,714,608; 2,714,609; and 2,714,610, all issued to M. Matter, disclose similar polyethoxy esters.

Similarly, U.S. Pat. No. 5,090,914, issued Feb. 25, 1992 to D. T. Reardan et al., discloses poly(oxyalkylene) aromatic compounds having an amino or hydrazinocarbonyl substituent on the aromatic moiety and an ester, amide, carbamate, urea or ether linking group between the aromatic moiety and the poly(oxyalkylene) moiety. These compounds are taught to be useful for modifying macromolecular species such as proteins and enzymes. U.S. Pat. Nos. 5,081,295; 5,103,039; and 5,157,099; all issued to D. T. Reardan et al., disclose similar poly(oxyalkylene) aromatic compounds.

U.S. Pat. No. 4,328,322, issued Sept. 22, 1980 to R. C. Baron, discloses amino- and nitrobenzoate esters of oligomeric polyols, such as poly(ethylene) glycol. These materials are used in the production of synthetic polymers by reaction with a polyisocyanate. Similar materials are disclosed in U.S. Pat. No. 4,515,981, issued May 7, 1985 to K. Otani et al., and in U.S. Pat. Nos. 5,039,775 and 5,086,153, both issued to Y. Oyaizu.

It has now been discovered that poly(oxyalkylene) aromatic esters having a nitro, amino, N-alkylamino or N,N-dialkylamino substituent on the aromatic moiety are surprisingly useful for reducing engine deposits, especially intake valve deposits, when employed as fuel additives in fuel compositions.

SUMMARY OF THE INVENTION

The present invention provides a novel fuel composition comprising a major amount of hydrocarbons boiling in the gasoline or diesel range and an effective deposit-controlling amount of a poly(oxyalkylene) aromatic ester having the formula:

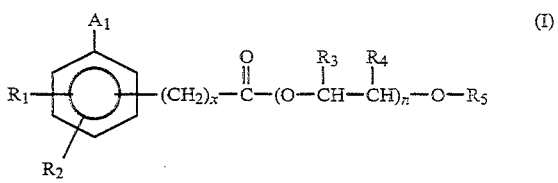

wherein $A_1$ is nitro, amino, N-alkylamino wherein the alkyl group contains 1 to 6 carbon atoms, or N,N-dialkylamino wherein each alkyl group independently contains 1 to 6 carbon atoms; $R_1$ and $R_2$ are independently hydrogen, hydroxy, lower alkyl having 1 to 6 carbon atoms, or lower alkoxy having 1 to 6 carbon atoms; $R_3$ and $R_4$ are independently hydrogen or lower alkyl having 1 to 6 carbon atoms and each $R_3$ and $R_4$ is independently selected in each $-O-CHR_3-CHR_4-$ unit; $R_5$ is hydrogen, alkyl having 1 to 100 carbon atoms, phenyl, aralkyl having 7 to 100 carbon atoms or alkaryl having 7 to 100 carbon atoms, or an acyl group of the formula:

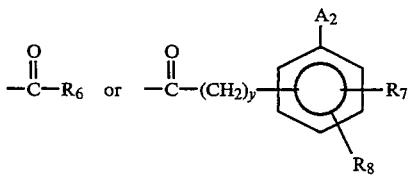

wherein $R_6$ is alkyl having 1 to 30 carbon atoms, phenyl, aralkyl having 7 to 36 carbon atoms or alkaryl having 7 to 36 carbon atoms; $R_7$ and $R_8$ are independently hydrogen, hydroxy, lower alkyl having 1 to 6 carbon atoms, or lower alkoxy having 1 to 6 carbon atoms; $A_2$ is a nitro, amino, N-alkylamino wherein the alkyl group contains 1 to 6 carbon atoms, or N,N-dialkylamino wherein each alkyl group independently contains 1 to 6 carbon atoms; n is an integer from 5 to 100; and x and y are each independently integers from 0 to 10.

The present invention further provides a fuel concentrate comprising an inert stable oleophilic organic solvent boiling in the range of from about 150° F. (65° C.) to 400° F. (205° C.) and from about 10 to 70 weight percent of a poly(oxyalkylene) aromatic ester of formula I above.

The present invention also provides a method for reducing engine deposits in an internal combustion engine comprising operating the engine with a fuel composition containing an effective deposit-controlling amount of a poly(oxyalkylene) aromatic ester of formula I above.

The present invention additionally provides novel poly(oxyalkylene) aromatic esters having the formula:

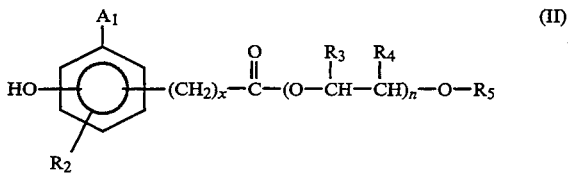

wherein $A_1$, $R_2$, $R_3$, $R_4$, $R_5$, n and x are as defined above.

Among other factors, the present invention is based on the discovery that poly(oxyalkylene) aromatic esters having a nitro, amino, N-alkylamino or N,N-dialkylamino substituent on the aromatic moiety are surprisingly useful for reducing engine deposits, especially on intake valves, when employed as fuel additives in fuel compositions.

DETAILED DESCRIPTION OF THE INVENTION

The fuel compositions provided by the present invention contain a major amount of hydrocarbons boiling in the gasoline or diesel range and an effective deposit-controlling amount of a poly(oxyalkylene) aromatic ester having the general formula:

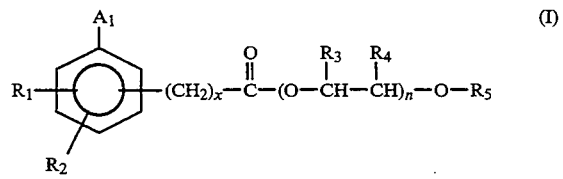

wherein $A_1$, $R_1$, $R_2$, $R_3$, $R_4$, $R_5$, n and x are as defined above.

In formula I, $A_1$ is preferably a nitro, amino, or N-alkylamino group. More preferably, $A_1$ is a nitro or amino group. Most preferably, $A_1$ is an amino group.

Preferably, $R_1$ is hydrogen, hydroxy, or lower alkyl having 1 to 4 carbon atoms. More preferably, $R_1$ is hydrogen or hydroxy. Most preferably, $R_1$ is hydroxy.

$R_2$ is preferably hydrogen.

Preferably, one of $R_3$ and $R_4$ is lower alkyl having 1 to 3 carbon atoms and the other is hydrogen. More preferably, one of $R_3$ and $R_4$ is methyl or ethyl and the other is hydrogen. Most preferably, one of $R_3$ and $R_4$ is ethyl and the other is hydrogen.

$R_5$ is preferably hydrogen, alkyl having 1 to 30 carbon atoms, or alkylphenyl having an alkyl group containing 1 to 30 carbon atoms. More preferably, $R_5$ is hydrogen, alkyl having 2 to 24 carbon atoms, or alkylphenyl having an alkyl group containing 2 to 24 carbon atoms. Still more preferably, $R_5$ is hydrogen, alkyl having 4 to 12 carbon atoms or alkylphenyl having an alkyl group containing 4 to 12 carbon atoms. Most preferably, $R_5$ is alkylphenyl having an alkyl group containing 4 to 12 carbon atoms.

$R_6$ is preferably alkyl having 4 to 12 carbon atoms.

Preferably, $R_7$ is hydrogen, hydroxy, or lower alkyl having 1 to 4 carbon atoms. More preferably, $R_7$ is hydrogen or hydroxy. Most preferably, $R_7$ is hydroxy.

$R_8$ is preferably hydrogen.

Preferably, $A_2$ is a nitro, amino or N-alkylamino group. More preferably, $A_2$ is a nitro or amino group. Most preferably, $A_2$ is an amino group.

When either $A_1$ or $A_2$ is an N-alkylamino group, the alkyl group of the N-alkylamino moiety preferably contains 1 to 4 carbon atoms. More preferably, the alkyl group is methyl or ethyl. For example, particularly preferred N-alkylamino groups are N-methylamino and N-ethylamino groups.

Similarly, when either $A_1$ or $A_2$ is an N,N-dialkylamino group, each alkyl group of the N,N-dialkylamino moiety preferably contains 1 to 4 carbon atoms. More preferably, each alkyl group is either methyl or ethyl. For example, particularly preferred N,N-dialkylamino groups are N,N-dimethylamino, N-ethyl-N-methylamino and N,N-diethylamino groups.

Preferably, n is an integer from 8 to 50. More preferably, n is an integer from 10 to 30. Preferably, x is an integer from 0 to 2. Most preferably, x is 0. Preferably, y is an integer from 0 to 2. Most preferably, y is 0.

A preferred group of poly(oxyalkylene) aromatic esters for use in this invention are compounds of formula I wherein $A_1$ is amino or nitro; $R_1$ is hydrogen or hydroxy; $R_2$ is hydrogen; one of $R_3$ and $R_4$ is hydrogen and the other is methyl or ethyl; $R_5$ is hydrogen, alkyl having 1 to about 30 carbon atoms or alkylphenyl having an alkyl group containing 1 to about 30 carbon atoms; n is 8 to 50 and x is 0, 1 or 2.

A more preferred group of poly(oxyalkylene) aromatic esters are those of formula I wherein $A_1$ is amino or nitro; $R_1$ is hydrogen or hydroxy; $R_2$ is hydrogen; one of $R_3$ and $R_4$ is hydrogen and the other is methyl or ethyl; $R_5$ is hydrogen, alkyl having 2 to 24 carbon atoms or alkylphenyl having an alkyl group containing 2 to 24 carbon atoms; n is 8 to 50; and x is 0.

A particularly preferred group of poly(oxyalkylene) aromatic esters are those of formula I wherein $A_1$ is amino or nitro; $R_1$ is hydroxy; $R_2$ is hydrogen; one of $R_3$ and $R_4$ is hydrogen and the other is methyl or ethyl; $R_5$ is hydrogen, alkyl having 2 to 24 carbon atoms or alkylphenyl having an alkyl group containing 2 to 24 carbon atoms; n is 8 to 50; and x is 0.

An especially preferred group of poly(oxyalkylene) aromatic esters have the formula:

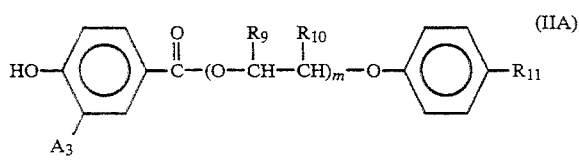

wherein $A_3$ is amino or nitro; one of $R_9$ and $R_{10}$ is methyl or ethyl and the other is hydrogen; $R_{11}$ is an alkyl group having 2 to 24 carbon atoms; and m is an integer from 8 to 50.

It is especially preferred that the nitro, amino, N-alkylamino or N,N-dialkylamino substituent present in the aromatic moiety of the poly(oxyalkylene) aromatic esters of this invention be situated in a meta or para position relative to the poly(oxyalkylene) ester moiety. When the aromatic moiety also contains a hydroxyl substituent, it is particularly preferred that this hydroxyl group be in a meta or para position relative to the poly(oxyalkylene) ester moiety and in an ortho position relative to the nitro, amino, N-alkylamino or N,N-dialkylamino substituent.

The poly(oxyalkylene) aromatic esters employed in the present invention will generally have a sufficient molecular weight so as to be non-volatile at normal engine intake valve operating temperatures (about 200°–250° C.). Typically, the molecular weight of the poly(oxyalkylene) aromatic esters will range from about 600 to about 10,000, preferably from 1,000 to 3,000.

Generally, the poly(oxyalkylene) aromatic esters employed in this invention will contain an average of about 5 to about 100 oxyalkylene units; preferably, 8 to 50 oxyalkylene units; more preferably, 10 to 30 oxyalkylene units.

Fuel-soluble salts of the poly(oxyalkylene) aromatic esters employed in the present invention can be readily prepared for those compounds containing an amino, N-alkylamino or N,N-dialkylamino group and such salts are contemplated to be useful for preventing or controlling engine deposits. Suitable salts include, for example, those obtained by protonating the amino moiety with a strong organic acid, such as an alkyl- or arylsulfonic acid. Preferred salts are derived from toluenesulfonic acid and methanesulfonic acid.

Definitions

As used herein the following terms have the following meanings unless expressly stated to the contrary.

The term "amino" refers to the group: —$NH_2$.

The term "N-alkylamino" refers to the group: —$NHR_a$ wherein $R_a$ is an alkyl group The term "N,N-dialkylamino" refers to the group: —$NR_bR_c$, wherein $R_b$ and $R_c$ are alkyl groups.

The term "alkyl" refers to both straight- and branched-chain alkyl groups.

The term "lower alkyl" refers to alkyl groups having 1 to about 6 carbon atoms and includes primary, secondary and tertiary alkyl groups. Typical lower alkyl groups include, for example, methyl, ethyl, n-propyl, isopropyl, n-butyl, sec-butyl, t-butyl, n-pentyl, n-hexyl and the like.

The term "lower alkoxy" refers to the group —$OR_d$ wherein $R_d$ is lower alkyl. Typical lower alkoxy groups include methoxy, ethoxy, and the like.

The term "alkaryl" refers to the group:

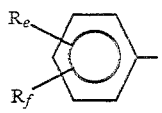

wherein $R_e$ and $R_f$ are each independently hydrogen or an alkyl group, with the proviso that both $R_e$ and $R_f$ are not hydrogen. Typical alkaryl groups include, for example, tolyl, xylyl, cumenyl, ethylphenyl, butylphenyl, dibutylphenyl, hexylphenyl, octylphenyl, dioctylphenyl, nonylphenyl, decylphenyl, didecylphenyl, dodecylphenyl, hexadecylphenyl, octadecylphenyl, icosylphenyl, tricontylphenyl and the like. The term "alkylphenyl" refers to an alkaryl group of the above formula in which $R_e$ is alkyl and $R_f$ is hydrogen.

The term "aralkyl" refers to the group:

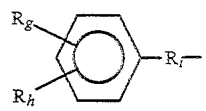

wherein $R_g$ and $R_h$ are each independently hydrogen or an alkyl group; and $R_i$ is an alkylene group. Typical alkaryl groups include, for example, benzyl, methylbenzyl, dimethylbenzyl, phenethyl, and the like.

The term "oxyalkylene unit" refers to an ether moiety having the general formula:

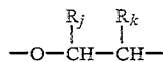

wherein $R_j$ and $R_k$ are each independently hydrogen or lower alkyl groups.

The term "poly(oxyalkylene)" refers to a polymer or oligomer having the general formula:

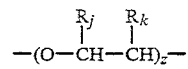

wherein $R_j$ and $R_k$ are as defined above, and z is an integer greater than 1. When referring herein to the number of poly(oxyalkylene) units in a particular poly(oxyalkylene) compound, it is to be understood that this number refers to the average number of poly(oxyalkylene) units in such compounds unless expressly stated to the contrary.

General Synthetic Procedures

The poly(oxyalkylene) aromatic esters employed in this invention can be prepared by the following general methods and procedures. Those skilled in the art will recognize that where typical or preferred process conditions (e.g. reaction temperatures, times, mole ratios of reactants, solvents, pressures, etc.) are given, other process conditions may also be used unless otherwise stated. Optimum reaction conditions may vary with the particular reactants or solvents used, but one skilled in the art will be able to determine such conditions by routine optimization procedures.

Moreover, those skilled in the art will recognize that it may be necessary to block or protect certain functional groups while conducting the following synthetic procedures. In such cases, the protecting group will serve to protect the functional group from undesired reactions or to block its undesired reaction with other functional groups or with the reagents used to carry out the desired chemical transformations. The proper choice of a protecting group for a particular functional group will be readily apparent to one skilled in the art. Various protecting groups and their introduction and removal are described, for example, in T. W. Greene and P. G. M. Wuts, *Protective Groups in Organic Synthesis,* Second Edition, Wiley, New York, 1991, and references cited therein.

In the present synthetic procedures, a hydroxyl group will preferably be protected, when necessary, as the benzyl or tert-butyldimethylsilyl ether. Introduction and removal of these protecting groups is well described in the art. Amino groups may also require protection and this may be accomplished by employing a standard amino protecting group, such as a benzyloxycarbonyl or a trifluoroacetyl group. Additionally, as will be discussed in further detail hereinbelow, the poly(oxyalkylene) aromatic esters of this invention having an amino group on the aromatic moiety will generally be prepared from the corresponding nitro derivative. Accordingly, in many of the following procedures, a nitro group will serve as a protecting group for the amino moiety.

The poly(oxyalkylene) aromatic esters of the present invention having the formula:

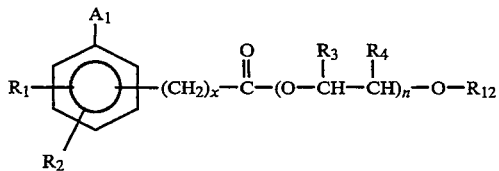
(III)

wherein $A_1$, $R_1$–$R_4$, n and x are as defined above and $R_{12}$ is an alkyl, phenyl, aralkyl or alkaryl group, may be prepared by esterifying an aromatic carboxylic acid having the formula:

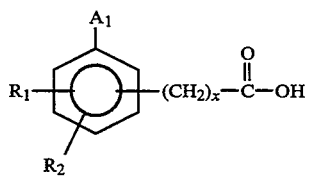
(IV)

with a poly(oxyalkylene) alcohol having the formula:

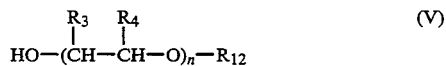
(V)

using conventional esterification reaction conditions.

This reaction is typically conducted by contacting poly(oxyalkylene) alcohol V with about 0.90 to about 1.5 molar equivalents of aromatic carboxylic acid IV in the presence of acidic catalyst at a temperature in the range of 70° C. to about 160° C. for about 0.5 to about 48 hours. Suitable acid catalysts for this reaction include, for example, p-toluenesulfonic acid, methanesulfonic acid, sulfuric acid and the like. The reaction may be conducted in the presence or absence of an inert solvent, such as toluene, xylene and the like. The water generated during this reaction may be continuously removed by conventional procedures, such as azeotropic distillation with an inert solvent, such as xylene.

Alternatively, the poly(oxyalkylene) aromatic esters of formula III may be prepared by reacting poly(oxyalkylene) alcohol V with an acid halide derived from aromatic carboxylic acid IV, such as an acid chloride or acid bromide.

Generally, the carboxylic acid moiety of IV may be converted into an acyl halide moiety by contacting IV with an inorganic acid halide, such as thionyl chloride, phosphorous trichloride, phosphorous tribromide, or phosphorous pentachloride; or with oxalyl chloride. Typically, this reaction will be conducted using about 1 to 5 molar equivalents of the inorganic acid halide or oxalyl chloride, either neat or in an inert solvent, such as diethyl ether, at a temperature in the range of about 20° C. to about 80° C. for about 1 to about 48 hours. A catalyst, such as N,N-dimethylformamide, may also be used in this reaction.

Reaction of the acid halide derived from IV with poly(oxyalkylene) alcohol V provides a poly(oxyalkylene) aromatic ester of formula III. Typically, this reaction is conducted by contacting V with about 0.9 to about 1.5 molar equivalents of the acid halide in an inert solvent, such as toluene, dichloromethane, diethyl ether, and the like, at a temperature in the range of about 25° C. to about 150° C. The reaction is generally complete in about 0.5 to about 48 hours. Preferably, the reaction is conducted in the presence of a sufficient amount of an amine capable of neutralizing the acid generated during the reaction, such as triethylamine, di(isopropyl)ethylamine, pyridine or 4-dimethylaminopyridine.

The aromatic carboxylic acids of formula IV employed in the above-described procedures are either known compounds or can be prepared from known compounds by conventional procedures. Representative aromatic carboxylic acids suitable for use in these reactions include, for example, 2-aminobenzoic acid (anthranilic acid), 3-aminobenzoic acid, 4-aminobenzoic acid, 3-amino-4-hydroxybenzoic acid, 4-amino-3-hydroxybenzoic acid, 3-aminophenylacetic acid, 4-aminophenylacetic acid, 3-amino-4-methoxybenzoic acid, 4-amino-3-methoxybenzoic acid, 4-amino-3-methylbenzoic acid, 4-amino-3,5-di-t-butylbenzoic acid, 2-nitrobenzoic acid, 3-nitrobenzoic acid, 4-nitrobenzoic acid, 2-nitrophenylacetic acid, 3-nitrophenylacetic acid, 4-nitrophenylacetic acid, 3-hydroxy-4-nitrobenzoic acid, 4-hydroxy-3-nitrobenzoic acid, 4-hydroxy-3-nitrophenylacetic acid, 3-(N-methylamino)benzoic acid, 4-(N-methylamino)-benzoic acid, 3-(N-ethylamino)benzoic acid, 4-(N-ethylamino)benzoic acid, 3-(N,N-dimethylamino)benzoic acid, 4-(N,N-dimethylamino)benzoic acid and the like.

Preferred aromatic carboxylic acids include 3-aminobenzoic acid, 4-aminobenzoic acid, 3-amino-4-hydroxybenzoic acid, 4-amino-3-hydroxybenzoic acid, 3-nitrobenzoic acid, 4-nitrobenzoic acid, 3-hydroxy-4-nitrobenzoic acid and 4-hydroxy-3-nitrobenzoic acid.

The poly(oxyalkylene) alcohols of formula V are also known compounds that can be prepared using conventional procedures. For example, suitable procedures for preparing such compounds are taught in U.S. Pat. Nos. 2,782,240 and 2,841,479, the disclosures of which are incorporated herein by reference.

Preferably, the poly(oxyalkylene) alcohols of formula V are prepared by contacting an alkoxide or phenoxide metal salt having the formula:

$$R_{12}OM \qquad (VI)$$

wherein $R_{12}$ is as defined above and M is a metal cation, such as lithium, sodium, potassium and the like, with about 5 to about 100 molar equivalents of an alkylene oxide (an epoxide) having the formula:

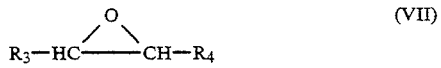
(VII)

wherein $R_3$ and $R_4$ are as defined above.

Typically, metal salt VI is prepared by contacting the corresponding hydroxy compound $R_{12}OH$ with a strong base, such as sodium hydride, potassium hydride, sodium amide and the like, in an inert solvent, such as toluene, xylene and the like, under substantially anhydrous conditions at a temperature in the range from about $-10°$ C. to about $120°$ C. for about 0.25 to about 3 hours.

Metal salt VI is generally not isolated, but is reacted in situ with alkylene oxide VII to provide, after neutralization, the poly(oxyalkylene) alcohol V. This polymerization reaction is typically conducted in a substantially anhydrous inert solvent at a temperature of about $30°$ C. to about $150°$ C. for about 2 to about 120 hours. Suitable solvents for this reaction, include toluene, xylene and the like. Typically, the reaction is conducted at a pressure sufficient to contain the reactants and the solvent, preferably at atmospheric or ambient pressure.

The amount of alkylene oxide employed in this reaction will generally depend on the number of oxyalkylene units desired in the product. Typically, the molar ratio of alkylene oxide VII to metal salt VI will range from about 5:1 to about 100:1; preferably, from 8:1 to 50:1, more preferably from 10:1 to 30:1.

Alkylene oxides suitable for use in this polymerization reaction include, for example, ethylene oxide; propylene oxide; butylene oxides, such as 1,2-butylene oxide (1,2-epoxybutane) and 2,3-butylene oxide (2,3-epoxybutane); pentylene oxides; hexylene oxides; octylene oxides and the like. Preferred alkylene oxides are propylene oxide and 1,2-butylene oxide.

In the polymerization reaction, a single type of alkylene oxide may be employed, e.g. propylene oxide, in which case the product is a homopolymer, e.g. a poly(oxypropylene) polymer. Copolymers are equally satisfactory and random copolymers can be prepared by contacting metal salt VI with a mixture of alkylene oxides, such as a mixture of propylene oxide and 1,2-butylene oxide, under polymerization conditions. Copolymers containing blocks of oxyalkylene units are also suitable for use in this invention. Block copolymers can be prepared by contacting metal salt VI with first one alkylene oxide, then others in any order, or repetitively, under polymerization conditions.

Poly(oxyalkylene) copolymers prepared by terminating or capping the poly(oxyalkylene) moiety with 1 to 10 oxyethylene units, preferably 2 to 5 oxyethylene units, are particularly useful in the present invention, since these copolymers have been found to be more readily esterified than those having an alkyl branch in the terminal oxyalkylene unit. These copolymers may be prepared by contacting metal salt IV with an alkylene oxide of formula VII, such as 1,2-butylene oxide or propylene oxide, under polymerization conditions and then capping or terminating the resulting block of oxyalkylene units with oxyethylene units by adding ethylene oxide.

The poly(oxyalkylene) alcohol V may also be prepared by living or immortal polymerization as described by S. Inoue and T. Aida in *Encyclopedia of Polymer Science and Engineering,* Second Edition, Supplemental Volume, J. Wiley and Sons, New York, pages 412–420 (1989). These procedures are especially useful for preparing poly(oxyalkylene) alcohols of formula V in which $R_3$ and $R_4$ are both alkyl groups.

As noted above, the alkoxide or phenoxide metal salt VI used in the above procedures is generally derived from the corresponding hydroxy compound, $R_{12}OH$. Suitable hydroxy compounds include straight- or branched-chain aliphatic alcohols having 1 to about 100 carbon atoms and phenols having the formula:

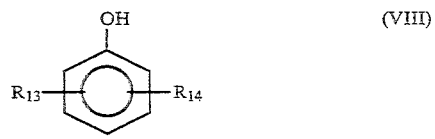
(VIII)

wherein $R_{13}$ is an alkyl group having 1 to about 100 carbon atoms and $R_{14}$ is hydrogen; or $R_{13}$ and $R_{14}$ are both alkyl groups, each independently containing 1 to about 50 carbon atoms.

Representative examples of straight- or branched-chain aliphatic alcohols suitable for use in this invention include, but are not limited to, n-butanol; isobutanol; sec-butanol; t-butanol; n-pentanol; n-hexanol; n-heptanol; n-octanol; isooctanol; n-nonanol; n-decanol; n-dodecanol; n-hexadecanol (cetyl alcohol); n-octadecanol (stearyl alcohol); alcohols derived from linear $C_{10}$ to $C_{30}$ alpha olefins and mixtures thereof; and alcohols derived from polymers of $C_2$ to $C_6$ olefins, such as alcohols derived from polypropylene and polybutene, including polypropylene alcohols having 9 to about 100 carbon atoms and polybutylene alcohols having to about 100 carbon atoms. Preferred straight- or branched-chain aliphatic alcohols will contain 1 to about carbon atoms, more preferably 2 to about 24 carbon atoms, and most preferably 4 to 12 carbon atoms.

Particularly preferred aliphatic alcohols are butanols.

The phenols of formula VIII may be monoalkyl-substituted phenols or dialkyl-substituted phenols. Monoalkyl-substituted phenols are preferred, especially monoalkylphenols having an alkyl substituent in the para position.

Preferably, the alkyl group of the alkylphenol will contain 1 to about 30 carbon atoms, more preferably 2 to 24 carbon atoms, and most preferably 4 to 12 carbon atoms. Representative examples of phenols suitable for use in this invention include, but are not limited to, phenol, methylphenol, dimethylphenol, ethylphenol, butylphenol, octylphenol, decylphenol, dodecylphenol, tetradecylphenol, hexadecylphenol, octadecylphenol, eicosylphenol, tetracosylphenol, hexacosylphenol, triacontylphenol and the like. Also, mixtures of alkylphenols may be employed, such as a mixture of $C_{14}$-$C_{18}$ alkylphenols, a mixture of $C_{18}$-$C_{24}$ alkylphenols, a mixture of $C_{20}$-$C_{24}$ alkylphenols, or a mixture of $C_{16}$-$C_{26}$ alkylphenols.

Particularly preferred alkylphenols are prepared by alkylating phenol with polymers or oligomers of $C_3$ to $C_6$ olefins, such as polypropylene or polybutene. These polymers typically contain 8 to about 100 carbon atoms, preferably 10 to 30 carbon atoms. An especially preferred alkylphenol is prepared by alkylating phenol with a propylene polymer having an average of 4 units. This polymer has the common name of propylene tetramer and is commercially available.

The poly(oxyalkylene) aromatic esters of formula I wherein $R_5$ is hydrogen, i.e. compounds having the formula:

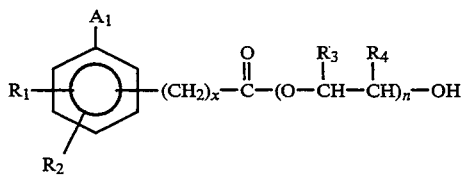

wherein $A_1$, $R_1$-$R_4$, n and x are as defined above, may be prepared from compounds of formula III wherein $R_{12}$ is a labile hydrocarbyl group, such as a benzyl or t-butyl group, by removing the hydrocarbyl group under appropriate conditions to provide a hydroxyl group. For example, compounds of formula III where $R_{12}$ represents a benzyl group may be prepared by employing a metal salt VI derived from benzyl alcohol in the above-described synthetic procedures. Cleavage of the benzyl ether using conventional hydrogenolysis procedures then provides a compound of formula IX. Other labile hydrocarbyl groups, such as a t-butyl group, may be similarly employed for those compounds having functional groups that are not compatible with hydrogenolysis conditions, such as nitro groups. t-Butyl ethers may be cleaved under acidic conditions using, for example, trifluoroacetic acid.

The poly(oxyalkylene) aromatic esters of formula I wherein $R_5$ is an acyl group, i.e. compounds having the formula:

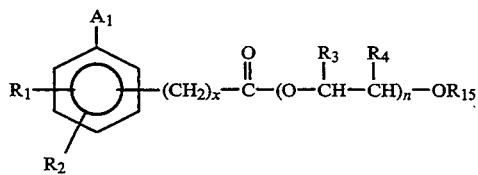

wherein $A_1$, $R_1$-$R_4$, n and x are as defined above and $R_{15}$ is an acyl group having the formula:

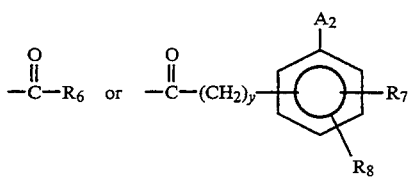

wherein $A_2$, $R_6$-$R_8$ and y are as defined above, may be synthesized from a compound of formula IX by acylating the terminal hydroxyl group of the poly(oxyalkylene) moiety with a suitable acylating agent.

Acylating agents suitable for use in this reaction include acid halides, such as acid chlorides and bromides; and carboxylic acid anhydrides. Preferred acylating agents include those having the formula: $R_6C(O)$—X, wherein $R_6$ is alkyl having 1 to 30, preferably 4 to 12 carbon atoms, phenyl, aralkyl having 7 to 36 carbon atoms or alkaryl having 7 to 36 carbon atoms, and X is chloro or bromo; and the acid halide derivatives of aromatic carboxylic acid IV described hereinabove.

Representative examples of preferred acylating agents having the formula $R_6C(O)$—X include acetyl chloride, propionyl chloride, butanoyl chloride, pivaloyl chloride, octanoyl chloride, decanoyl chloride and the like.

Typically, acylation of IX is conducted by contacting IX with about 0.95 to about 1.2 molar equivalents of the acylating agent in an inert solvent, such as toluene, dichloromethane, diethyl ether and the like, at a temperature in the range of about 25° C. to about 150° C. for about 0.5 to about 48 hours. When an acid halide is employed as the acylating agent, the reaction is preferably conducted in the presence of a sufficient amount of an amine capable of neutralizing the acid generated during the reaction, such as triethylamine, di(isopropyl)ethylamine, pyridine or 4-dimethylamino-pyridine.

A preferred group of poly(oxyalkylene) aromatic esters of formula X are those having the same aromatic ester group at each end the poly(oxyalkylene) moiety, i.e. compounds of formula X wherein $R_{15}$ is an acyl group having the formula:

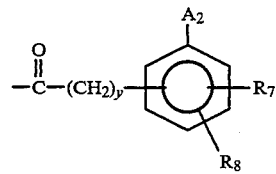

wherein $A_2=A_1$; $R_7=R_1$; $R_8=R_2$; and x and y are the same integer.

These compounds may be prepared from a poly(oxyalkylene) diol having the formula:

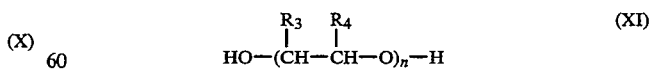

wherein $R_3$, $R_4$, and n are as defined above, by esterifying each of the hydroxyl groups present in XI with a aromatic carboxylic acid of formula IV or an acyl halide derivative thereof using the above-described synthetic procedures. The poly(oxyalkylene) diols of formula XI are commercially available or may be prepared by conventional procedures, for example, by using sodium or potassium hydroxide in place of the alkoxide or phenoxide metal salt VI in the above-described alkylene oxide polymerization reaction.

When synthesizing the poly(oxyalkylene) aromatic esters of formula I having an amino group on the aromatic moiety (i.e. where $A_1$ is an amino group), it is generally desirable to first prepare the corresponding nitro compound (i.e. where $A_1$ is a nitro group) using the above-described synthetic procedures, and then to reduce the nitro group to an amino group using conventional procedures. Aromatic nitro groups may be reduced to amino groups using a number of procedures that are well known in the art. For example, aromatic nitro groups may be reduced under catalytic hydrogenation conditions; or by using a reducing metal, such as zinc, tin, iron and the like, in the presence of an acid, such as dilute hydrochloric acid.

Generally, reduction of the nitro group by catalytic hydrogenation is preferred. Typically, this reaction is conducted using about 1 to 4 atmospheres of hydrogen and a platinum or palladium catalyst, such as palladium on carbon. The reaction is typically carried out at a temperature of about 0° C. to about 100° C. for about 1 to 24 hours in an inert solvent, such as ethanol, ethyl acetate and the like. Hydrogenation of aromatic nitro groups is discussed in further detail in, for example, P. N. Rylander, *Catalytic Hydrogenation in Organic Synthesis*, pp. 113-137, Academic Press (1979); and Organic Synthesis, Collective Vol. I, Second Edition, pp. 240-241, John Wiley & Sons, Inc. (1941); and references cited therein.

Fuel Compositions

The poly(oxyalkylene) aromatic esters of the present invention are useful as additives in hydrocarbon fuels to prevent and control engine deposits, particularly intake valve deposits. Typically, the desired deposit control is achieved by operating an internal combustion engine with a fuel composition containing a poly(oxyalkylene) aromatic ester of the present invention. The proper concentration of additive necessary to achieve the desired level of deposit control varies depending upon the type of fuel employed, the type of engine, and the presence of other fuel additives.

In general, the concentration of the poly(oxyalkylene) aromatic esters of this invention in hydrocarbon fuel will range from about 50 to about 2500 parts per million (ppm) by weight, preferably from 75 to 1,000 ppm. When other deposit control additives are present, a lesser amount of the present additive may be used.

The poly(oxyalkylene) aromatic esters of the present invention may also be formulated as a concentrate using an inert stable oleophilic (i.e., dissolves in gasoline) organic solvent boiling in the range of about 150° F. to 400° F. (about 65° C. to 205° C.). Preferably, an aliphatic or an aromatic hydrocarbon solvent is used, such as benzene, toluene, xylene or higher-boiling aromatics or aromatic thinners. Aliphatic alcohols containing about 3 to 8 carbon atoms, such as isopropanol, isobutylcarbinol, n-butanol and the like, in combination with hydrocarbon solvents are also suitable for use with the present additives. In the concentrate, the amount of the additive will generally range from about 10 to about 70 weight percent, preferably to 50 weight percent, more preferably from 20 to 40 weight percent.

In gasoline fuels, other fuel additives may be employed with the additives of the present invention, including, for example, oxygenates, such as t-butyl methyl ether, antiknock agents, such as methylcyclopentadienyl manganese tricarbonyl, and other dispersants/detergents, such as hydrocarbyl amines, hydrocarbyl poly(oxyalkylene) amines, or succinimides. Additionally, antioxidants, metal deactivators and demulsifiers may be present.

In diesel fuels, other well-known additives can be employed, such as pour point depressants, flow improvers, cetane improvers, and the like.

A fuel-soluble, nonvolatile carrier fluid or oil may also be used with the poly(oxyalkylene) aromatic esters of this invention. The carrier fluid is a chemically inert hydrocarbon-soluble liquid vehicle which substantially increases the nonvolatile residue (NVR), or solvent-free liquid fraction of the fuel additive composition while not overwhelmingly contributing to octane requirement increase. The carrier fluid may be a natural or synthetic oil, such as mineral oil, refined petroleum oils, synthetic polyalkanes and alkenes, including hydrogenated and unhydrogenated polyalphaolefins, synthetic polyoxyalkylene-derived oils, such as those described, for example, in U.S. Pat. No. 4,191,537 to Lewis, and polyesters, such as those described, for example, in U.S. Pat. Nos. 3,756,793 and 5,004,478 to Robinson and Vogel et al., respectively, and in European Patent Application Nos. 356,726 and 382,159, published Mar. 7, 1990 and Aug. 16, 1990, respectively.

These carrier fluids are believed to act as a carrier for the fuel additives of the present invention and to assist in removing and retarding deposits. The carrier fluid may also exhibit synergistic deposit control properties when used in combination with a poly(oxyalkylene) aromatic ester of this invention.

The carrier fluids are typically employed in amounts ranging from about 100 to about 5000 ppm by weight of the hydrocarbon fuel, preferably from 400 to 3000 ppm of the fuel. Preferably, the ratio of carrier fluid to deposit control additive will range from about 0.5:1 to about 10:1, more preferably from 1:1 to 4:1, most preferably about 2:1.

When employed in a fuel concentrate, carrier fluids will generally be present in amounts ranging from about 20 to about 60 weight percent, preferably from 30 to 50 weight percent.

EXAMPLES

The following examples are presented to illustrate specific embodiments of the present invention and synthetic preparations thereof; and therefore these examples should not be interpreted as limitations upon the scope of this invention.

Example 1

Preparation of α-(3-Hydroxy-4-nitrobenzoyl)-ω-4-dodecylphenoxypoly(oxybutylene)

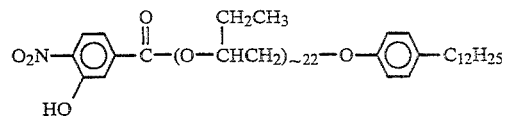

To a flask equipped with a magnetic stirrer, thermometer, Dean-Stark trap, nitrogen inlet and reflux condenser was added 5.94 grams of 3-hydroxy-4-nitrobenzoic acid, 50.0 grams α-hydroxy-ω-4-dodecylphenoxypoly(oxybutylene) having an average of oxybutylene units (prepared essentially as described in Example 6 of U.S. Pat. No. 4,160,648) and 0.47 grams of p-toluenesulfonic acid. The reaction was heated to 130° C. for 48 hours and then cooled to room temperature. Diethyl ether (750 mL) was added and the organic phase was washed twice with saturated aqueous sodium bicarbonate, and once with saturated aqueous sodium chloride solution. The organic layer was then dried over anhydrous magnesium sulfate, filtered and concentrated in vacuo to afford 50.7 grams of a black oil. The oil contained 80% of the desired product and 20% unreacted α-hydroxy-ω-4-dodecylphenoxypoly(oxybutylene) as determined by $^1$H NMR analysis. The product had an average of oxybutylene units. IR (neat) 1722 cm$^{-1}$; $^1$H NMR (CDCl$_3$) δ 10.5 (s, 1H), 8.2, 7.6 (AB quartet, 2H), 7.8 (s, 1H), 7.0–7.25 (m, 2H), 6.65–6.8 (m, 2H), 5.1–5.25 (m, 1H), 3.85–4.0 (m, 2H), 3.1–3.85 (m, 63H), 0.55–1.75 (m, 135H).

Similarly, by using the above procedures and the appropriate starting materials and reagents, the following compounds can be prepared:

α-(3-hydroxy-4-nitrobenzoyl)-ω-4-butyloxypoly(oxybutylene);

α-(3-hydroxy-4-nitrobenzoyl)-ω-4-hexyloxypoly(oxybutylene);

α-(3-hydroxy-4-nitrobenzoyl)-ω-4-octyloxypoly(oxybutylene);

α-(3-hydroxy-4-nitrobenzoyl)-ω-4-decyloxypoly(oxybutylene);

α-(3-hydroxy-4-nitrobenzoyl)-ω-4-dodecyloxypoly(oxybutylene);

α-(3-hydroxy-4-nitrobenzoyl)-ω-4-octylphenoxypoly(oxybutylene);

α-(3-hydroxy-4-nitrobenzoyl)-ω-4-octadecylphenoxypoly(oxybutylene);

α-(3-hydroxy-4-nitrobenzoyl)-ω-4-eicosylphenoxypoly(oxybutylene);

α-(3-hydroxy-4-nitrobenzoyl)-ω-4-tetracosylphenoxypoly(oxybutylene);

α-(3-hydroxy-4-nitrobenzoyl)-ω-4-(C$_{18}$–C$_{24}$ alkyl )phenoxypoly(oxybutylene);

α-(3-hydroxy-4-nitrobenzoyl)-ω-4-butyloxypoly(oxypropylene); and

α-(3-hydroxy-4-nitrobenzoyl)-ω-4-dodecylphenoxypoly(oxypropylene).

Example 2

Preparation of α-(4-Hydroxy-3-nitrobenzoyl)-107-4-dodecylphenoxpoly(oxybutylene)

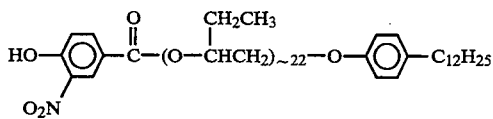

The procedure of Example 1 was repeated using 4-hydroxy-3-nitrobenzoic acid instead of 3-hydroxy-4-nitrobenzoic acid to provide 45.8 grams of a black oil. The oil was found to contain 60% of the desired product and 40% unreacted α-hydroxy-ω-4-dodecylphenoxypoly(oxybutylene) by $^1$H NMR analysis. The product had an average of 22 oxybutylene units. IR (neat) 1722 cm$^{-1}$); $^1$H NMR (CDCl$_3$) δ 10.8 (s, 1H), 8.8 (s, 1H), 8.25 (d, 1H), 7.1–7.25 (m, 3H), 6.7–6.8 (m, 2H), 5.1–5.25 (m, 1H), 3.85–4.0 (m, 2H), 3.1–3.85 (m, 63H), 0.6–1.8 (m, 135H).

Similarly, by using the above procedures and the appropriate starting materials and reagents, the following compounds can be prepared:

α-(4-hydroxy-3-nitrobenzoyl)-ω-4-butyloxypoly(oxybutylene);

α-(4-hydroxy-3-nitrobenzoyl)-ω-4-hexyloxypoly(oxybutylene);

α-(4-hydroxy-3-nitrobenzoyl)-ω-4-octyloxypoly(oxybutylene);

α-(4-hydroxy-3-nitrobenzoyl)-ω-4-decyloxypoly(oxybutylene);

α-(4-hydroxy-3-nitrobenzoyl)-ω-4-dodecyloxypoly(oxybutylene);

α-(4-hydroxy-3-nitrobenzoyl)-ω-4-octylphenoxypoly(oxybutylene);

α-(4-hydroxy-3-nitrobenzoyl)-ω-4-octadecylphenoxypoly(oxybutylene);

α-(4-hydroxy-3-nitrobenzoyl)-ω-4-eicosylphenoxypoly(oxybutylene);

α-(4-hydroxy-3-nitrobenzoyl)-ω-4-tetracosylphenoxypoly(oxybutylene);

α-(4-hydroxy-3-nitrobenzoyl)-ω-4-(C$_{18}$–C$_{24}$ alkyl)-phenoxypoly(oxybutylene);

α-(4-hydroxy-3-nitrobenzoyl)-ω-4-butyloxypoly(oxypropylene); and

α-(4-hydroxy-3-nitrobenzoyl)-ω-4-dodecylphenoxypoly(oxypropylene).

Example 3

Preparation of α-(4-Nitrobenzoyl)-ω-4-dodecylphenoxypoly(oxybutylene)

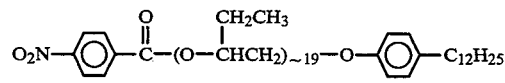

4-Nitrobenzoyl chloride (16.89 grams) was combined with 150.43 grams of α-hydroxy-ω-4-dodecylphenoxypoly(oxybutylene) having an average of 19 oxybutylene units (prepared essentially as described in Example 6 of U.S. Pat. No. 4,160,648) and 200 mL of anhydrous toluene. Triethylamine (13.4 mL) and 4-dimethylaminopyridine (5.57 grams) were then added and the resulting mixture was heated to reflux under nitrogen for 16 hours. The reaction was cooled to room temperature and diluted with 600 mL of diethyl ether. The organic layer was washed twice with 1% aqueous hydrochloric acid, twice with saturated aqueous sodium bicarbonate solution, and once with saturated aqueous sodium chloride. The organic layer was then dried over anhydrous magnesium sulfate, filtered and the solvents removed in vacuo to yield 157.1 grams of a yellow oil. The product had an average of oxybutylene units. IR (neat) 1722 cm$^{-1}$; $^1$H NMR (CDCl$_3$) δ 8.3, 8.2 (AB quartet, 4H), 7.1–7.3 (m, 2H), 6.75–6.85 (m, 2H), 5.15–5.3 (m, 1H), 3.85–4.0 (m, 2H), 3.1–3.85 (m, 54H), 0.6–1.8 (m, 120H).

Similarly, by using the above procedures and the appropriate starting materials and reagents, the following compounds can be prepared:

-(4-nitrobenzoyl)-ω-4-butyloxypoly(oxybutylene);
-(4-nitrobenzoyl)-ω-4-hexyloxypoly(oxybutylene);
-(4-nitrobenzoyl)-ω-4-octyloxypoly(oxybutylene);
-(4-nitrobenzoyl)-ω-4-decyloxypoly(oxybutylene);
-(4-nitrobenzoyl)-ω-4-dodecyloxypoly(oxybutylene);
-(4-nitrobenzoyl)-ω-4-octylphenoxypoly(oxybutylene);

-(4-nitrobenzoyl)-ω-4-octadecylphenoxypoly(oxybutylene);
-(4-nitrobenzoyl)-ω-4-eicosylphenoxypoly(oxybutylene);
-(4-nitrobenzoyl)-ω-4-tetracosylphenoxypoly(oxybutylene);
-(4-nitrobenzoyl)-ω-4-(C$_{18}$-C$_{24}$ alkyl)phenoxypoly(oxybutylene);
-(4-nitrobenzoyl)-ω-4-butyloxypoly(oxypropylene); and
-(4-nitrobenzoyl)-ω-4-dodecylphenoxypoly(oxypropylene).

Example 4

Preparation of 4-(N,N-Dimethylamino)benzoyl Chloride Hydrochloride

To a flask equipped with a magnetic stirrer and a drying tube was added 10.0 grams of 4-(N,N-dimethylamino)benzoic acid, 150 mL of anhydrous dichloromethane, 1 mL of anhydrous dimethylformamide and then 13.2 mL of oxalyl chloride. The resulting mixture was stirred at room temperature for 16 hours and then the solvents removed in vacuo to yield the desired acid chloride.

Example 5

Preparation of α-(4-(N,N-Dimethylamino)benzoyl)-ω-4-dodecylphenoxypoly(oxybutylene)

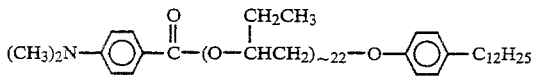

4-(N,N-Dimethylamino)benzoyl chloride hydrochloride (10.0 grams) was combined with 101.63 grams of α-hydroxy-ω-4-dodecylphenoxypoly(oxybutylene) having an average of 22 oxybutylene units (prepared essentially as described in Example 6 of U.S. Pat. No. 4,160,648) and 240 mL of anhydrous toluene. Triethylamine (15.6 mL) and 4-dimethylamino pyridine (3.33 grams) were then added and the resulting mixture was heated to reflux under nitrogen for 16 hours. The reaction was cooled to room temperature and diluted with 750 mL of diethyl ether. The organic layer was washed twice with 1% aqueous hydrochloric acid, twice with saturated aqueous sodium bicarbonate solution, and once with saturate aqueous sodium chloride. The organic layer was then dried over anhydrous magnesium sulfate, filtered and the solvents removed in vacuo to yield 9.7 grams of the desired product as a yellow oil. The product had an average of 22 oxybutylene units. $^1$H NMR (CDCl$_3$) δ 7.95, 6.65 (AB quartet, 4H), 7.1–7.25 (m, 2H), 6.8–6.9 (m, 2H), 5.05–5.2 (m, 1H), 3.9–4.05 (m, 2H), 3.2–3.9 (m, 63H), 3.05 (s, 6H), 0.5–1.9 (m, 135H).

Example 6

Preparation of α-(4-Aminobenzoyl)-ω-4-dodecylphenoxypoly(oxybutylene)

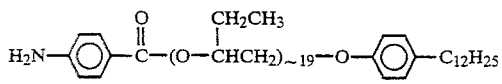

A solution of 100.5 grams of the product from Example 3 in 220 mL of ethyl acetate containing 7.0 grams of 10% palladium on charcoal was hydrogenated at 35–40 psi for 16 hours on a Parr low-pressure hydrogenator. Catalyst filtration and removal of the solvent in vacuo yielded 96.36 grams of the desired product as a colorless oil. The product had an average of 19 oxybutylene units. IR (neat) 1709 cm$^{-1}$; $^1$H NMR (CDCl$_3$) δ 7.9, 6.65 (AB quartet, 4H), 7.05–7.25 (m, 2H), 6.7–6.9 (m, 2H), 5.05–5.15 (m, 1H), 4.0–4.1 (bs, 2H), 3.85–4.0 (m, 2H), 3.1–3.85 (m, 54), 0.6–1.8 (m, 120H).

Similarly, by using the above procedures and the appropriate starting materials and reagents, the following compounds can be prepared:
-(4-aminobenzoyl)-ω-4-butyloxypoly(oxybutylene);
-(4-aminobenzoyl)-ω-4-hexyloxypoly(oxybutylene);
-(4-aminobenzoyl)-ω-4-octyloxypoly(oxybutylene);
-(4-aminobenzoyl)-ω-4-decyloxypoly(oxybutylene);
-(4-aminobenzoyl)-ω-4-dodecyloxypoly(oxybutylene);
-(4-aminobenzoyl)-ω-4-octylphenoxypoly(oxybutylene);
-(4-aminobenzoyl)-ω-4-octadecylphenoxypoly(oxybutylene);
-(4-aminobenzoyl)-ω-4-eicosylphenoxypoly(oxybutylene);
-(4-aminobenzoyl)-ω-4-tetracosylphenoxypoly(oxybutylene);
-(4-aminobenzoyl)-ω-4-(C$_{18}$C$_{24}$ alkyl)phenoxypoly(oxybutylene);
-(4-aminobenzoyl)-ω-4-butyloxypoly(oxypropylene); and
-(4-aminobenzoyl)-ω-4-dodecylphenoxypoly(oxypropylene).

Example 7

Preparation of α-(4-Amino-3-hydroxybenzoyl)-ω-4-dodecylphenoxypoly(oxybutylene)

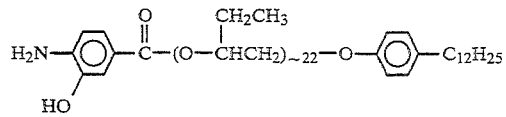

The product of Example 1 was hydrogenated as described in Example 6 to provide the desired product. The product had an average of oxybutylene units. IR (neat) 1709 cm$^{-1}$; $^1$H NMR (CDCl$_3$) δ 7.4–7.55 (m, 2H), 7.05–7.2 (m, 2H), 6.75–6.85 (m, 2H), 6.65 (d, 1H), 5.0–5.15 (m, 1H), 3.85–4.05 (m, 24), 3.05–3.85 (m, 63H), 0.6–1.8 (m, 135H).

Similarly, by using the above procedures and the appropriate starting materials and reagents, the following compounds can be prepared:
-(4-amino-3-hydroxybenzoyl)-ω-4-butyloxypoly(oxybutylene);
-(4-amino-3-hydroxybenzoyl)-ω-4-hexyloxypoly(oxybutylene);
-(4-amino-3-hydroxybenzoyl)-ω-4-octyloxypoly(oxybutylene);
-(4-amino-3-hydroxybenzoyl)-ω-4-decyloxypoly(oxybutylene);
-(4-amino-3-hydroxybenzoyl)-ω-4-dodecyloxypoly(oxybutylene);
-(4-amino-3-hydroxybenzoyl)-ω-4-octylphenoxypoly(oxybutylene);
-(4-amino-3-hydroxybenzoyl)-ω-4-octadecylphenoxypoly(oxybutylene);
-(4-amino-3-hydroxybenzoyl)-ω-4-eicosylphenoxypoly(oxybutylene);

-(4-amino-3-hydroxybenzoyl)-ω-4-tetracosylphenoxypoly(oxybutylene);
-(4-amino-3-hydroxybenzoyl)-ω-4-($C_{18}$-$C_{24}$ alkyl)-phenoxypoly(oxybutylene);
-(4-amino-3-hydroxybenzoyl)-ω-4-butyloxypoly(oxypropylene);and
-(4-amino-3-hydroxybenzoyl)-ω-4-dodecylphenoxypoly(oxypropylene).

Example 8

Preparation of
α-(3-Amino-4-hydroxybenzoyl)-ω-4-dodecylphenoxypoly(oxybutylene).

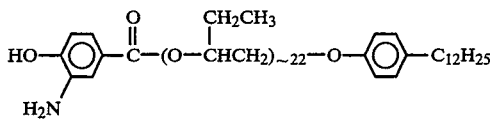

The product of Example 2 was hydrogenated as described in Example 6 to provide the desired product. The product had an average of 22 oxybutylene units. IR (neat) 1709 cm$^{-1}$; $^1$H NMR (CDCl$_3$) δ 7.35–7.45 (m, 2H), 7.05–7.30 (m, 2H), 6.65–6.9 (m, 3H), 5.0–5.2 (m, 1H), 3.8–4.0 (m, 2H), 3.05–3.8 (m, 63H), 0.5–1.75 (m, 135H).

Similarly, by using the above procedures and the appropriate starting materials and reagents, the following compounds can be prepared:
-(3-amino-4-hydroxybenzoyl)-ω-4-butyloxypoly(oxybutylene);
-(3-amino-4-hydroxybenzoyl)-ω-4-hexyloxypoly(oxybutylene);
-(3-amino-4-hydroxybenzoyl)-ω-4-octyloxypoly(oxybutylene);
-(3-amino-4-hydroxybenzoyl)-ω-4-decyloxypoly(oxybutylene);
-(3-amino-4-hydroxybenzoyl)-ω-4-dodecyloxypoly(oxybutylene);
-(3-amino-4-hydroxybenzoyl)-ω-4-octylphenoxypoly(oxybutylene);
-(3-amino-4-hydroxybenzoyl)-ω-4-octadecylphenoxypoly(oxybutylene);
-(3-amino-4-hydroxybenzoyl)-ω-4-eicosylphenoxypoly(oxybutylene);
-(3-amino-4-hydroxybenzoyl)-ω-4-tetracosylphenoxypoly(oxybutylene);
-(3-amino-4-hydroxybenzoyl)-ω-4-($C_{18}$-$C_{24}$ alkyl)-phenoxypoly(oxybutylene);
-(3-amino-4-hydroxybenzoyl)-ω-4-butyloxypoly(oxypropylene);and
-(3-amino-4-hydroxybenzoyl)-ω-4-dodecylphenoxypoly(oxypropylene).

Comparative Example A

Preparation of
α-(Benzoyl)-ω-4-dodecylphenoxypoly(oxybutylene)

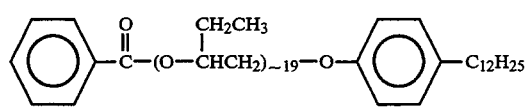

The procedure of Example 3 was repeated using benzoyl chloride instead of 4-nitrobenzoyl chloride to provide a yellow oil. The oil was chromatographed on silica gel, eluting with hexane/diethyl ether/ethanol (70:25:5) to afford the desired product as a light yellow oil. The product had an average of oxybutylene groups. IR (neat) 1715 cm$^{-1}$; $^1$H NMR (CDCl$_3$) δ 8.1 (d, 2H), 7.5–7.65 (m, 1H), 7.3–7.5 (m, 2H), 7.1–7.25 (m, 2H), 6.75–6.85 (m, 2H), 5.1–5.2 (m, 1H), 3.8–4.0 (m, 2H), 3.1–3.8 (m, 54H), 0.6–1.8 (m, 120H).

Example 9

Single-Cylinder Engine Test

The test compounds were blended in gasoline and their deposit reducing capacity determined in an ASTM/CFR single-cylinder engine test.

A Waukesha CFR single-cylinder engine was used. Each run was carried out for hours, at the end of which time the intake valve was removed, washed with hexane and weighed. The previously determined weight of the clean valve was subtracted from the weight of the value at the end of the run. The differences between the two weights is the weight of the deposit. A lesser amount of deposit indicates a superior additive. The operating conditions of the test were as follows: water jacket temperature 200° F.; vacuum of 12 in Hg, air-fuel ratio of 12, ignition spark timing of 40° BTC; engine speed is 1800 rpm; the crankcase oil is a commercial 30 W oil.

The amount of carbonaceous deposit in milligrams on the intake valves is reported for each of the test compounds in Table I.

TABLE I

| Sample[1] | Intake Valve Deposit Weight (in milligrams) | | |
|---|---|---|---|
| | Run 1 | Run 2 | Average |
| Base Fuel | 168.0 | 179.2 | 173.6 |
| Example 1 | 36.0 | 31.7 | 33.9 |
| Example 2 | 21.0 | 27.3 | 24.2 |
| Example 3 | 45.3 | 57.8 | 51.6 |
| Example 5 | 133.0 | 124.9 | 129.0 |
| Example 6 | 30.4 | 31.4 | 30.9 |
| Example 7 | 33.5 | 36.4 | 35.0 |
| Example 8 | 0.0 | 0.5 | 0.3 |
| Comp. Exam. A | 201.0 | 207.4 | 204.2 |

[1]At 200 parts per million actives (ppma).

The base fuel employed in the above single-cylinder engine tests was a regular octane unleaded gasoline containing no fuel detergent. The test compounds were admixed with the base fuel to give a concentration of 200 ppma (parts per million actives).

The data in Table I illustrates the significant reduction in intake valve deposits provided by the poly(oxyalkylene) aromatic esters of the present invention (Examples 1–3 and 5–8) compared to the base fuel and the poly(oxyalkylene) aromatic ester of Comparative Example A.

Example 10

Multicylinder Engine Test

The poly(oxyalkylene) aromatic esters of the present invention were tested in a laboratory multicylinder engine to evaluate their intake valve and combustion chamber deposit control performance. The test engine was a 4.3 liter, TBI (throttle body injected), V6 engine manufactured by General Motors Corporation. The major engine dimensions are set forth in Table II:

TABLE II

| Engine Dimensions | |
|---|---|
| Bore | 10.16 cm |

TABLE II-continued

| Engine Dimensions | |
|---|---|
| Stroke | 8.84 cm |
| Displacement Volume | 4.3 liter |
| Compression Ratio | 9.3:1 |

The test engine was operated for 40 hours (24 hours a day) on a prescribed load and speed schedule representative of typical driving conditions.

The cycle for engine operation during the test is set forth in Table III.

TABLE III

Engine Driving Cycle

| Step | Mode | Time in Mode [Sec][1] | Dynamometer Load [kg] | Engine Speed [RPM] |
|---|---|---|---|---|
| 1 | Idle | 60 | 0 | 800 |
| 2 | City Cruise | 150 | 10 | 1,500 |
| 3 | Acceleration | 40 | 25 | 2,800 |
| 4 | Heavy HWY Cruise | 210 | 15 | 2,200 |
| 5 | Light HWY Cruise | 60 | 10 | 2,200 |
| 6 | Idle | 60 | 0 | 800 |
| 7 | City Cruise | 180 | 10 | 1,500 |
| 8 | Idle | 60 | 0 | 800 |

[1] All steps, except step number 3, include a 15 second transition ramp. Step 3 includes a 20 second transition ramp.

All of the test runs were made with the same base gasoline, which was representative of commercial unleaded fuel. The results are set forth in Table IV.

TABLE IV

Multicylinder Engine Test Results

| Sample[1] | | Intake Valve Deposits[2] | Combustion Chamber Deposits[2] |
|---|---|---|---|
| Base Fuel | Run 1 | 962 | 2059 |
| | Run 2 | 710 | 2339 |
| | Average | 836 | 2199 |
| Example 8 | Run 1 | 135 | 2561 |
| | Run 2 | 210 | 2511 |
| | Average | 173 | 2536 |

[1] At 200 parts per million actives (ppma).
[2] In milligrams (mg).

The base fuel employed in the above multicylinder engine tests contained no fuel detergent. The test compounds were admixed with the base fuel to give a concentration of 200 ppma (parts per million actives).

The data in Table IV illustrates the significant reduction in intake valve deposits provided by the poly(oxyalkylene) aromatic ester of the present invention (Example 8) compared to the base fuel.

What is claimed is:

1. A fuel composition comprising a major amount of hydrocarbons boiling in the gasoline or diesel range and an effective deposit-controlling amount of a compound of the formula:

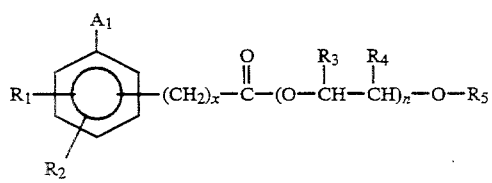

wherein $A_1$ is nitro, amino, N-alkylamino wherein the alkyl group contains 1 to 6 carbon atoms, or N,N-dialkylamino wherein each alkyl group independently contains 1 to 6 carbon atoms;

$R_1$ and $R_2$ are independently hydrogen, hydroxy, lower alkyl having 1 to 6 carbon atoms, or lower alkoxy having 1 to 6 carbon atoms;

$R_3$ and $R_4$ are independently hydrogen or lower alkyl having 1 to 6 carbon atoms and each $R_3$ and $R_4$ is independently selected in each —O—$CHR_3$—CH$R_4$— unit;

$R_5$ is hydrogen, alkyl having 1 to 100 carbon atoms, phenyl, aralkyl having 7 to 100 carbon atoms, alkaryl having 7 to 100 carbon atoms, or an acyl group having the formula:

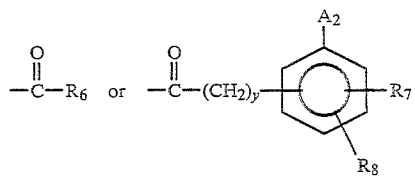

wherein $R_6$ is alkyl having 1 to 30 carbon atoms, phenyl, aralkyl having 7 to 36 carbon atoms or alkaryl having 7 to 36 carbon atoms;

$R_7$ and $R_8$ are independently hydrogen, hydroxy, lower alkyl having 1 to 6 carbon atoms, or lower alkoxy having 1 to 6 carbon atoms;

$A_2$ is nitro, amino, N-alkylamino wherein the alkyl group contains 1 to 6 carbon atoms, or N,N-dialkylamino wherein each alkyl group independently contains 1 to 6 carbon atoms;

n is an integer from 5 to 100; and x and y are each independently integers from 0 to 10.

2. The fuel composition according to claim 1 wherein n is an integer ranging from 8 to 50.

3. The fuel composition according to claim 2 wherein n is an integer ranging from 10 to 30.

4. The fuel composition according to claim 2 wherein $R_1$ is hydrogen, hydroxy, or lower alkyl having 1 to 4 carbon atoms; and $R_2$ is hydrogen.

5. The fuel composition according to claim 4 wherein $R_5$ is hydrogen, alkyl having 1 to 30 carbon atoms, or alkylphenyl having an alkyl group containing 1 to 30 carbon atoms.

6. The fuel composition according to claim 5 wherein $R_1$ is hydrogen or hydroxy.

7. The fuel composition according to claim 6 wherein $A_1$ is nitro or amino.

8. The fuel composition according to claim 7 wherein $R_5$ is hydrogen, alkyl having 2 to 24 carbon atoms, or alkylphenyl having an alkyl group containing 2 to 24 carbon atoms.

9. The fuel composition according to claim 8 wherein one of $R_3$ and $R_4$ is lower alkyl having 1 to 3 carbon atoms and the other is hydrogen.

10. The fuel composition according to claim 9 wherein one of $R_3$ and $R_4$ is methyl or ethyl and the other is hydrogen.

11. The fuel composition according to claim 10 wherein x is 0, 1 or 2.

12. The fuel composition according to claim 11 wherein $R_1$ is hydroxy, $R_5$ is alkylphenyl having an alkyl group containing 4 to 12 carbon atoms, and x is 0.

13. The fuel composition according to claim 12 wherein $A_1$ is amino.

14. The fuel composition according to claim 1 wherein said composition contains about 50 to about 2500 parts per million by weight of said compound.

15. The fuel composition according to claim 14 wherein said composition further contains about 100 to about 5000 parts per million by weight of a fuel soluble, non-volatile carrier fluid.

16. A method for reducing engine deposits in an internal combustion engine comprising operating an internal combustion engine with the fuel composition of claim 1.

17. A fuel concentrate comprising an inert stable oleophilic organic solvent boiling in the range of from about 150° F. to 400° F. and from about 10 to about 70 weight percent of a compound of the formula:

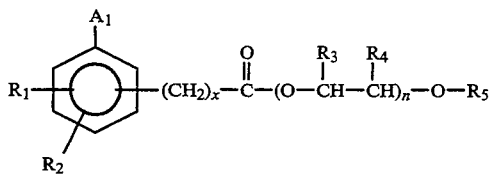

wherein $A_1$ is nitro, amino, N-alkylamino wherein the alkyl group contains 1 to 6 carbon atoms, or N,N-dialkylamino wherein each alkyl group independently contains 1 to 6 carbon atoms;

$R_1$ and $R_2$ are independently hydrogen, hydroxy, lower alkyl having 1 to 6 carbon atoms, or lower alkoxy having 1 to 6 carbon atoms;

$R_3$ and $R_4$ are independently hydrogen or lower alkyl having 1 to 6 carbon atoms and each $R_3$ and $R_4$ is independently selected in each —O—CHR$_3$—CHR$_4$— unit;

$R_5$ is hydrogen, alkyl having 1 to 100 carbon atoms, phenyl, aralkyl having 7 to 100 carbon atoms, alkaryl having 7 to 100 carbon atoms, or an acyl group having the formula:

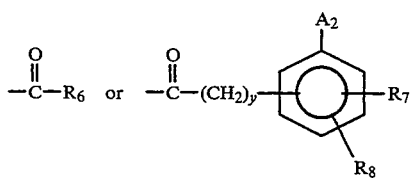

wherein $R_6$ is alkyl having 1 to 30 carbon atoms, phenyl, aralkyl having 7 to 36 carbon atoms or alkaryl having 7 to 36 carbon atoms;

$R_7$ and $R_8$ are independently hydrogen, hydroxy, lower alkyl having 1 to 6 carbon atoms, or lower alkoxy having 1 to 6 carbon atoms;

$A_2$ is nitro, amino, N-alkylamino wherein the alkyl group contains 1 to 6 carbon atoms, or N,N-dialkylamino wherein each alkyl group independently contains 1 to 6 carbon atoms;

n is an integer from 5 to 100; and x and y are each independently integers from 0 to 10.

18. The fuel concentrate according to claim 17 wherein $A_1$ is amino or nitro; $R_1$ is hydrogen or hydroxy; $R_2$ is hydrogen; one of $R_3$ and $R_4$ is hydrogen and the other is methyl or ethyl; $R_5$ is hydrogen, alkyl having 1 to about 30 carbon atoms or alkylphenyl having an alkyl group containing 1 to about 30 carbon atoms; n is 8 to 50 and x is 0, 1 or 2.

19. The fuel concentrate according to claim 18 wherein $R_5$ is hydrogen, alkyl having 2 to about 24 carbon atoms or alkylphenyl having an alkyl group containing 2 to about 24 carbon atoms; and x is 0.

20. The fuel concentrate according to claim 19 wherein $A_1$ is amino; $R_1$ is hydroxy; and $R_5$ is alkyl phenyl having an alkyl group containing 4 to 12 carbon atoms.

21. A compound of the formula:

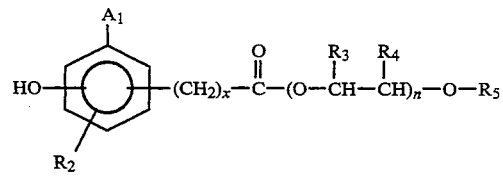

wherein $A_1$ is nitro, amino, N-alkylamino wherein the alkyl group contains 1 to 6 carbon atoms, or N,N-dialkylamino wherein each alkyl group independently contains 1 to 6 carbon atoms;

$R_2$ is hydrogen, hydroxy, lower alkyl having 1 to 6 carbon atoms, or lower alkoxy having 1 to 6 carbon atoms;

$R_3$ and $R_4$ are independently hydrogen or lower alkyl having 1 to 6 carbon atoms and each $R_3$ and $R_4$ is independently selected in each —O—CHR$_3$—CHR$_4$— unit;

$R_5$ is hydrogen, alkyl having 1 to 100 carbon atoms, phenyl, aralkyl having 7 to 100 carbon atoms, alkaryl having 7 to 100 carbon atoms, or an acyl group having the formula:

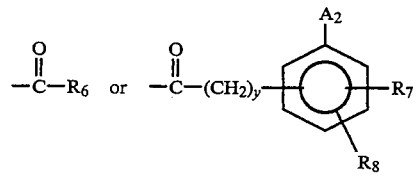

wherein $R_6$ is alkyl having 1 to 30 carbon atoms, phenyl, aralkyl having 7 to 36 carbon atoms or alkaryl having 7 to 36 carbon atoms;

$R_7$ and $R_8$ are independently hydrogen, hydroxy, lower alkyl having 1 to 6 carbon atoms, or lower alkoxy having 1 to 6 carbon atoms;

$A_2$ is nitro, amino, N-alkylamino wherein the alkyl group contains 1 to 6 carbon atoms, or N,N-dialkylamino wherein each alkyl group independently contains 1 to 6 carbon atoms;

n is an integer from 5 to 100; and x and y are each independently integers from 0 to 10.

22. The compound according to claim 21 wherein n is an integer ranging from 8 to 50.

23. The compound according to claim 22 wherein n is an integer ranging from 10 to 30.

24. The compound according to claim 22 wherein $R_2$ is hydrogen.

25. The compound according to claim 24 wherein $R_5$ is hydrogen, alkyl having 1 to 30 carbon atoms, or alkylphenyl having an alkyl group containing 1 to 30 carbon atoms.

26. The compound according to claim 25 wherein $A_1$ is nitro or amino.

27. The compound according to claim 26 wherein $R_5$ is hydrogen, alkyl having 2 to 24 carbon atoms, or alkylphenyl having an alkyl group containing 2 to 24 carbon atoms.

28. The compound according to claim 27 wherein one of $R_3$ and $R_4$ is lower alkyl having 1 to 3 carbon atoms and the other is hydrogen.

29. The compound according to claim 28 wherein one of $R_3$ and $R_4$ is methyl or ethyl and the other is hydrogen.

30. The compound according to claim 29 wherein x is 0, 1 or 2.

31. The compound according to claim 30 wherein $R_5$ is alkylphenyl having an alkyl group containing 4 to 12 carbon atoms, and x is 0.

32. The compound according to claim 31 wherein $A_1$ is amino.

* * * * *